(12) United States Patent
Thelen et al.

(10) Patent No.: US 8,835,361 B2
(45) Date of Patent: Sep. 16, 2014

(54) HIGH-THROUGHPUT QUANTITATION OF CROP SEED PROTEINS

(75) Inventors: Jay J. Thelen, Columbia, MO (US); Severin E. Stevenson, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 420 days.

(21) Appl. No.: 13/149,716

(22) Filed: May 31, 2011

(65) Prior Publication Data

US 2011/0294700 A1 Dec. 1, 2011

Related U.S. Application Data

(60) Provisional application No. 61/396,695, filed on Jun. 1, 2010.

(51) Int. Cl.

| | | |
|---|---|---|
| *C40B 30/10* | (2006.01) | |
| *A61K 38/00* | (2006.01) | |
| *C07K 2/00* | (2006.01) | |
| *C07K 4/00* | (2006.01) | |
| *C07K 5/00* | (2006.01) | |
| *C07K 7/00* | (2006.01) | |
| *C07K 14/00* | (2006.01) | |
| *C07K 16/00* | (2006.01) | |
| *C07K 17/00* | (2006.01) | |
| *G01N 33/68* | (2006.01) | |

(52) U.S. Cl.
CPC .................. *G01N 33/6848* (2013.01)
USPC ............................. 506/12; 530/300

(58) Field of Classification Search
None
See application file for complete search history.

(56) References Cited

U.S. PATENT DOCUMENTS

| 7,083,723 B2 * | 8/2006 | Tubbs et al. ............... 210/198.2 |
| 7,091,046 B2 * | 8/2006 | Monforte ...................... 436/173 |
| 7,183,118 B2 * | 2/2007 | Aebersold et al. ........... 436/173 |
| 7,195,751 B2 * | 3/2007 | Pappin et al. ................ 424/1.81 |
| 8,227,252 B2 | 7/2012 | Lawry et al. |
| 8,632,993 B2 * | 1/2014 | Moingeon et al. .............. 435/23 |
| 2007/0254371 A1 * | 11/2007 | Kas et al. ........................ 436/86 |

FOREIGN PATENT DOCUMENTS

WO    WO9841535    *    7/1998

OTHER PUBLICATIONS

Gonzalez-Buitrago et al. Proteomic approaches for identifying new allergens and diagnosing allergic diseases. Clinica Chimica Acta, 2007, vol. 385, pp. 21-27.*
Kuppannan et al., "Quantification and Characterization of Maize Lipid Transfer Protein, a Food Allergen, by Liquid Chromatography with Ultraviolet and Mass Spectrometric Detection," *Anal. Chem.*, 83(2):516-524, 2011.
Stevenson et al., "Monitoring changes in the proteome of transgenic peanuts engineered for reduced allergen content using ion trap quadrupole mass spectrometry," presentation given to American Society of Mass Spectrometry Meeting—Philadelphia on Jun. 1, 2009 (one page).
GenBank Accession No. AAU21499.2, oleosin 1 protein sequence from *Arachis hypogaea*, Aug. 25, 2006.
Stevenson et al., "Validation of gel-free, label-free quantitative proteomics approaches: Applications for seed allergen profiling," *J Proteomics*, 72(3):555-566, 2009.
Mooney et al., "High-throughput peptide mass fingerprinting of soybean seed proteins: automated workflow and utility of UniGene expressed sequence tag databases for protein identification," *Phytochemistry*, 65:1733-1744, 2004.

\* cited by examiner

*Primary Examiner* — Marcela M Cordero Garcia
(74) *Attorney, Agent, or Firm* — Dentons US LLP (57) ABSTRACT

The invention provides a high-throughput method for quantitating plant seed proteins, e.g. seed allergens. Such method involves obtaining a protein sample from the seed; analyzing the sample using mass spectrometry with a set of pre-designed internal standard peptides that are specific to the plant allergens; and monitoring frequencies and intensities of resulting spectra to obtain relative and absolute allergen contents in the seed. The invention also provides a system for high-throughput profiling of plant seed allergens. Such system comprises a set of pre-designed internal standard peptides that are specific to the plant seed allergens and one or more mass spectrometers.

18 Claims, 3 Drawing Sheets

```
                        SEQUENCE LISTING

<160> NUMBER OF SEQ ID NOS: 24

<210> SEQ ID NO 1
    <211> LENGTH: 13
    <212> TYPE: PRT
    <213> ORGANISM: Artificial sequence
    <220> FEATURE:
    <223> OTHER INFORMATION: Peptide internal standard specific to peanut
          allergen

<400> SEQUENCE: 1

Ala Asn Leu Arg Pro Cys Glu Gln His Leu Met Gln Lys
    1               5                   10

<210> SEQ ID NO 2
    <211> LENGTH: 10
    <212> TYPE: PRT
    <213> ORGANISM: Artificial sequence
    <220> FEATURE:
    <223> OTHER INFORMATION: Peptide internal standard specific to peanut
          allergen

<400> SEQUENCE: 2

Cys Asp Leu Glu Val Glu Ser Gly Gly Arg
    1               5                   10

<210> SEQ ID NO 3
    <211> LENGTH: 15
    <212> TYPE: PRT
    <213> ORGANISM: Artificial sequence
    <220> FEATURE:
    <223> OTHER INFORMATION: Peptide internal standard specific to peanut
          allergen

<400> SEQUENCE: 3

Gly Glu Asn Glu Ser Asp Glu Gln Gly Ala Ile Val Thr Val Arg
    1               5                   10                  15

<210> SEQ ID NO 4
    <211> LENGTH: 14
    <212> TYPE: PRT
    <213> ORGANISM: Artificial sequence
```

```
<220> FEATURE:
<223> OTHER INFORMATION: Peptide internal standard specific to peanut
      allergen

<400> SEQUENCE: 4

Thr Gln Pro His Thr Val Gln Val His Thr Thr Ala Gly Arg
1               5                   10

<210> SEQ ID NO 5
<211> LENGTH: 13
<212> TYPE: PRT
<213> ORGANISM: Artificial sequence
<220> FEATURE:
<223> OTHER INFORMATION: Peptide internal standard specific to peanut
      allergen

<400> SEQUENCE: 5

Cys Cys Asp Glu Leu Asp Gln Met Glu Asn Thr Glu Arg
1               5                   10

<210> SEQ ID NO 6
<211> LENGTH: 13
<212> TYPE: PRT
<213> ORGANISM: Artificial sequence
<220> FEATURE:
<223> OTHER INFORMATION: Peptide internal standard specific to soybean
      allergen

<400> SEQUENCE: 6

Val Leu Ile Val Pro Gln Asn Phe Val Val Ala Ala Arg
1               5                   10

<210> SEQ ID NO 7
<211> LENGTH: 18
<212> TYPE: PRT
<213> ORGANISM: Artificial sequence
<220> FEATURE:
<223> OTHER INFORMATION: Peptide internal standard specific to soybean
      allergen

<400> SEQUENCE: 7

Asn Leu Gln Gly Glu Asn Glu Glu Asp Ser Gly Ala Ile Val Thr
1               5                   10                  15

Val Lys

<210> SEQ ID NO 8
<211> LENGTH: 18
<212> TYPE: PRT
<213> ORGANISM: Artificial sequence
<220> FEATURE:
<223> OTHER INFORMATION: Peptide internal standard specific to soybean
      allergen

<400> SEQUENCE: 8

Phe Tyr Leu Ala Gly Asn Gln Glu Gln Glu Phe Leu Gln Tyr Gln Pro
1               5                   10                  15

Gln Lys

<210> SEQ ID NO 9
<211> LENGTH: 19
<212> TYPE: PRT
<213> ORGANISM: Artificial sequence
<220> FEATURE:
<223> OTHER INFORMATION: Peptide internal standard specific to soybean
      allergen

<400> SEQUENCE: 9
```

Val Glu Ser Glu Gly Gly Leu Ile Gln Thr Trp Asn Ser Gln His Pro
1               5                   10                  15

Glu Leu Lys

<210> SEQ ID NO 10
<211> LENGTH: 13
<212> TYPE: PRT
<213> ORGANISM: Artificial sequence
<220> FEATURE:
<223> OTHER INFORMATION: Peptide internal standard specific to soybean
      allergen

<400> SEQUENCE: 10

Leu Ile Thr Leu Ala Ile Pro Val Asn Lys Pro Gly Arg
1               5                   10

<210> SEQ ID NO 11
<211> LENGTH: 15
<212> TYPE: PRT
<213> ORGANISM: Artificial sequence
<220> FEATURE:
<223> OTHER INFORMATION: Peptide internal standard specific to soybean
      allergen

<400> SEQUENCE: 11

Ser Gln Ser Glu Ser Tyr Phe Val Asp Ala Gln Pro Gln Gln Lys
1               5                   10                  15

<210> SEQ ID NO 12
<211> LENGTH: 10
<212> TYPE: PRT
<213> ORGANISM: Artificial sequence
<220> FEATURE:
<223> OTHER INFORMATION: Peptide internal standard specific to soybean
      allergen

<400> SEQUENCE: 12

Val Leu Leu Gly Glu Glu Glu Glu Gln Arg
1               5                   10

<210> SEQ ID NO 13
<211> LENGTH: 11
<212> TYPE: PRT
<213> ORGANISM: Artificial sequence
<220> FEATURE:
<223> OTHER INFORMATION: Peptide internal standard specific to soybean
      allergen

<400> SEQUENCE: 13

Phe Ile Ala Glu Gly His Pro Leu Ser Leu Lys
1               5                   10

<210> SEQ ID NO 14
<211> LENGTH: 10
<212> TYPE: PRT
<213> ORGANISM: Artificial sequence
<220> FEATURE:
<223> OTHER INFORMATION: Peptide internal standard specific to soybean
      allergen

<400> SEQUENCE: 14

Val Ser Asp Asp Glu Phe Asn Asn Tyr Lys
1               5                   10

<210> SEQ ID NO 15
<211> LENGTH: 11

```
<212> TYPE: PRT
<213> ORGANISM: Artificial sequence
<220> FEATURE:
<223> OTHER INFORMATION: Peptide internal standard specific to soybean
      allergen

<400> SEQUENCE: 15

Asp Thr Val Asp Gly Trp Phe Asn Ile Glu Arg
1               5                   10

<210> SEQ ID NO 16
<211> LENGTH: 14
<212> TYPE: PRT
<213> ORGANISM: Artificial sequence
<220> FEATURE:
<223> OTHER INFORMATION: Peptide internal standard specific to soybean
      allergen

<400> SEQUENCE: 16

Asp Gly Pro Leu Glu Phe Phe Gly Phe Ser Thr Ser Ala Arg
1               5                   10

<210> SEQ ID NO 17
<211> LENGTH: 13
<212> TYPE: PRT
<213> ORGANISM: Artificial sequence
<220> FEATURE:
<223> OTHER INFORMATION: Peptide internal standard specific to soybean
      allergen

<400> SEQUENCE: 17

Asn Gly Leu His Leu Pro Ser Tyr Ser Pro Tyr Pro Arg
1               5                   10

<210> SEQ ID NO 18
<211> LENGTH: 10
<212> TYPE: PRT
<213> ORGANISM: Artificial sequence
<220> FEATURE:
<223> OTHER INFORMATION: Peptide internal standard specific to soybean
      allergen

<400> SEQUENCE: 18

Glu Glu Ser Glu Thr Leu Val Ser Ala Arg
1               5                   10

<210> SEQ ID NO 19
<211> LENGTH: 12
<212> TYPE: PRT
<213> ORGANISM: Artificial sequence
<220> FEATURE:
<223> OTHER INFORMATION: Peptide internal standard specific to soybean
      allergen

<400> SEQUENCE: 19

Ala Leu Val Thr Asp Ala Asp Asn Val Ile Pro Lys
1               5                   10

<210> SEQ ID NO 20
<211> LENGTH: 12
<212> TYPE: PRT
<213> ORGANISM: Artificial sequence
<220> FEATURE:
<223> OTHER INFORMATION: Peptide internal standard specific to soybean
      allergen

<400> SEQUENCE: 20

Leu Val Ala Gly Pro Asn Gly Gly Ser Ala Gly Lys
```

```
<210> SEQ ID NO 21
<211> LENGTH: 11
<212> TYPE: PRT
<213> ORGANISM: Artificial sequence
<220> FEATURE:
<223> OTHER INFORMATION: Peptide internal standard specific to soybean
      allergen

<400> SEQUENCE: 21

Gly Asp Ala Glu Pro Asn Gln Asp Glu Leu Lys
1               5                   10

<210> SEQ ID NO 22
<211> LENGTH: 14
<212> TYPE: PRT
<213> ORGANISM: Artificial sequence
<220> FEATURE:
<223> OTHER INFORMATION: Peptide specific to peanut allergen Oleosin 1

<400> SEQUENCE: 22

Phe Gly Asp Thr Ala Ala Gly Thr Asn Arg Tyr Pro Asp Arg
1               5                   10

<210> SEQ ID NO 23
<211> LENGTH: 20
<212> TYPE: PRT
<213> ORGANISM: Artificial sequence
<220> FEATURE:
<223> OTHER INFORMATION: Peptide specific to peanut allergen Oleosin 1

<400> SEQUENCE: 23

Phe Gly Asp Thr Ala Ala Gly Thr Asn Arg Tyr Pro Asp Arg Gly Pro
1               5                   10                  15

Ser Thr Ser Lys
            20

<210> SEQ ID NO 24
<211> LENGTH: 11
<212> TYPE: PRT
<213> ORGANISM: Artificial sequence
<220> FEATURE:
<223> OTHER INFORMATION: Peptide specific to peanut allergen Oleosin 1

<400> SEQUENCE: 24

Thr Lys Glu Val Gly Gln Glu Ile Gln Thr Lys
1               5                   10
```

HIGH-THROUGHPUT QUANTITATION OF CROP SEED PROTEINS

This application claims the priority of U.S. provisional application Ser. No. 61/396,695, filed Jun. 1, 2010, the entire disclosure of which is incorporated herein by reference.

BACKGROUND OF INVENTION

1. Field of the Invention

The present invention generally relates to plant protein screening. More specifically, the invention relates to a high-throughput method or system for quantifying plant seed proteins (e.g. plant allergens) based on mass spectrometry.

2. Background

Plant seeds, such as nuts and legumes, are the major provider of oils and bulk protein for the world, and new varieties are continually being created or discovered. However, plants seeds are also the major contributors of allergenic proteins that cause a majority of the reported cases of food-induced anaphylaxis. Thus, commercial and newly developed or discovered plants need to be screened for their relative and/or absolute allergen content before they are introduced into food products.

SUMMARY OF INVENTION

The invention provides a high-throughput method for quantitating allergens in a target plant seed using mass spectrometry. This method includes obtaining a protein sample from the seed; analyzing the sample using mass spectrometry with a set of pre-designed internal standard peptides that are specific for the plant allergen; and monitoring frequencies and intensities of resulting spectra to obtain relative and absolute allergen contents of the seed.

In one aspect of the present invention, internal standard peptides are designed through empirical analysis and in silico digestion analysis; synthesized chemically with a heavy amino acid residue or genetically by expressing a synthetic gene in the presence of stable isotope-labeled amino acid(s) or metabolic intermediates. In certain embodiments, the internal standards may be characterized individually by mass spectrometry (MS) analysis, including tandem mass spectrometry (MS/MS) analysis, more specifically, liquid chromatography-coupled tandem mass spectrometry analysis (LC-MS/MS). After characterization, pre-selected parameters of the peptides can be collected, such as LC retention time, optimal charge state, optimal collision energy to fragment the stable isotope-labeled peptide, and abundance of its product ions after fragmentation.

An exemplary list of stable isotope-labeled peptides is provided herein, which includes peptides comprising any one of SEQ ID NOs:1-5 or a combination thereof for peanut allergen quantitation, and peptides comprising any one of SEQ ID NOs:6-21 or a combination thereof for soybean allergen quantitation.

The invention also provides a high-throughput method for screening plant allergens within a food product, including any point during the process or the machines used to produce such products. Such method includes obtaining a sample from the food product or machine; analyzing the sample protein using mass spectrometry with a set of pre-designed internal standard peptides that are specific to the plant allergens; and monitoring frequencies and intensities of resulting spectra to obtain relative and absolute allergen contents in the food product.

The invention further provides a system for high-throughput profiling of plant seed allergens. Such system comprises a set of pre-designed internal standard peptides that are specific for the plant seed allergens; and one or more mass spectrometers.

BRIEF DESCRIPTION OF DRAWINGS

The following drawings form part of the present specification and are included to further demonstrate certain aspects of the invention. The invention may be better understood by reference to one or more of these drawings in combination with the detailed description of specific embodiments presented herein.

BRIEF DESCRIPTION OF SEQUENCES

SEQ ID NOs:1-5 are amino acid sequences of stable isotope-labeled peptides for peanut allergen quantitation.

SEQ ID NOs:6-21 are amino acid sequences of stable isotope-labeled peptides for soybean allergen quantitation.

SEQ ID NOs:22-24 are amino acid sequences of peptides specific to peanut allergen Oleosin 1.

DETAILED DESCRIPTION OF INVENTION

The invention provides a high-throughput, accurate, and cost effective method/system for quantifying plant seed allergens. The method/system are based on mass spectrometry with spectral counting and peak integration strategies and rationally designed synthetic peptides that are specific to the seed proteins as internal standards. The method/system is especially effective in screening and quantifying protein allergens for natural and genetically-modified crop seed and other food components.

The present method/system can be used to quantify a single peptide or can be multiplexed for the quantitation of multiple peptides, for example, in a single liquid chromatography-coupled tandem mass spectrometry analysis (LC-MS/MS) run. The upper limit of peptide multiplexing depends largely on the mass spectrometry instrumentation. The present method/system provide an effective and inexpensive workflow for quantifying prominent plant seed proteins beginning with intact, whole plant seed that does not require gel electrophoresis, antibodies, chemical labeling or a priori information about the seed to be analyzed. Additionally, the present method/system also provide the advantages of specific, absolute quantitation of known protein allergens, high quantitative accuracy, low analysis cost, and reduced analysis time.

In detail, the invention provides a high-throughput method and system for assessing the protein content of plant seed based on mass spectrometry with spectral counting and peak integration approaches and rationally designed synthetic peptides as internal standards. In certain embodiments, tandem mass spectrometry analysis, more specifically, liquid chromatography-coupled tandem mass spectrometry analysis (LC-MS/MS) is used. While spectral counting is generally considered a discovery and relative approach for protein quantitation, peak integration is generally associated with targeted peptide (protein) quantitation. Both approaches are generally needed for the development of a high-throughput, mass spectrometry-based assay for target proteins of interest. Spectral counting provides information on which peptides ionize well and are therefore suitable for quantitation in a targeted manner using peak integration. The invention employs this two-step approach in developing targeted assays for high-throughput profiling of plant proteins, such as seed allergens. Once suitable "proteotypic" peptides have been identified for a particular protein, it is possible to commerically synthesize a stable isotope-labeled peptide based upon the sequence of the ideal peptide. The stable isotope-labeled peptide is further used as an internal standard to quantitate in absolute terms the amount of the "proteotypic" peptide (a surrogate for the intact protein) in a biological sample.

In one embodiment, there is provided a method for quantitating allergens in a target plant seed. This method includes obtaining a protein sample from the seed; analyzing the sample using mass spectrometry with a set of pre-designed internal standard peptides that are specific to the allergen; and monitoring frequencies and intensities of resulting spectra to obtain relative and absolute allergen contents of the seed. In certain embodiments, tandem mass spectrometry analysis, more specifically, liquid chromatography-coupled tandem mass spectrometry analysis (LC-MS/MS) is used.

In the present invention, the series of internal standard peptides, i.e. stable isotope-labeled peptides, may be pre-designed, pre-synthesized and pre-characterized prior to use in the quantitation method. In one embodiment, the peptides are designed through two serial and iterative methods: empirical analysis and in silico digestion analysis. The empirical analysis method involves a fast scanning ion trap (e.g. the Thermo Fisher Scientific Inc. linear ion trap quadrupole), where total protein digests are surveyed for candidate peptides using "triple play"-type experiments. Triple-play experiments are untargeted analyses that search the ionized peptide pool as it elutes from the C18 reverse phase column. These experiments provide charged peptide masses and corresponding peptide sequence data. Peptides identified by protein identification software and correlated to proteins of interest (e.g. allergens) in these experiments are good candidates for an internal standard but must still be inspected for length, modifiable amino acids, internal as well as adjacent cleavage sites, and potential isobaric peptides determined by a translated genome query. Once selected, those peptides are considered specific for the proteins of interest.

The in silico digest analysis method can be employed when no ionizable peptide is experimentally observed. With this strategy the amino acid sequence for the protein of interest is analyzed whereby peptides are predicted using the cleavage rules for the appropriate chemical or protease. Rules for length, modifiable amino acids, adjacent cleavage residues, and non-isobaric peptides within the genespace also apply to this strategy.

In another embodiment, the internal standard peptides are synthesized either chemically with a heavy amino acid residue or genetically by expressing a synthetic, chimeric gene in the presence of stable isotope-labeled amino acid(s) or metabolic intermediates. In detail, the pre-designed peptides are further selected for ideal sequence length and composition. Particularly, peptides from 9-19 amino acids have been used effectively, while peptides with cysteines, methionines, tryptophan, histidines and multiple cleavage sites or internal cleavage sites are generally avoided to minimize mass alterations of the peptide by chemical modifications (like oxidation) or potential variable cleavage products. Then the pre-designed peptides are generated with a heavy amino acid and purified to >95%. The peptides may be commercially synthesized, or alternatively, recombinant expression of a synthetic gene fusion (concatenated peptides) in the presence of a stable isotope-labeled amino acid or metabolite may also be performed.

For example, the peptide internal standards for quantitating allergens in peanut and soybean are listed in Table 1 and Table 2, respectively, along with their sequences and isotopic masses.

TABLE 1

Peptides for peanut allergen quantitation

| SEQ ID NO | Peptide Name | Peptide Sequence | isotopic M+ H+ (unlabeled) | observed charge (+) | observed mass (Da-unlabeled) |
|---|---|---|---|---|---|
| 1 | Ara h 2 | ANLRPCEQHLMQK | 1567.783139 | 3.0 | 542.273051 |
| 2 | Ara h 2.02 | CDLEVESGGR | 1064.467678 | 2.0 | 561.248207 |
| 3 | Ara h 3/4 | GENESDEQGAIVTVR | 1603.755784 | 2.0 | 802.381530 |
| 4 | Oleosin | TQPHTVQVHTTAGR | 1532.792776 | 4.0 | 383.953651 |
| 5 | Ara h 6 | CCDELDQMENTER | 1585.592691 | 2.0 | 850.321444 |

TABLE 2

Peptides for soybean allergen quantitation

| SEQ ID NO | Peptide Name | Peptide Sequence | isotopic M+ H+ (unlabeled) | observed charge (+) | observed mass (Da-unlabeled) |
|---|---|---|---|---|---|
| 6 | Glycinin G1 | VLIVPQNFVVAAR | 1425.857604 | 2.0 | 713.432440 |
| 7 | Glycinin G2 | NLQGENEEEDSGAIVTVK | 1931.919212 | 2.0 | 966.463244 |
| 8 | Glycinin G3 | FYLAGNQEQEFLQYQPQK | 2231.076708 | 2.0 | 1116.041992 |
| 9 | Glycinin G4 | VESEGGLIQTWNSQHPELK | 2152.066872 | 3.0 | 718.027142 |
| 10 | Beta-conglycinin, α subunit | LITLAIPVNKPGR | 1391.873253 | 3.0 | 464.629269 |
| 11 | Beta-conglycinin, α' subunit | SQSESYFVDAQPQQK | 1741.802732 | 2.0 | 871.405004 |
| 12 | Beta-conglycinin, β subunit | VLLGEEEEQR | 1201.605879 | 2.0 | 601.306578 |
| 13 | Kunitz trypsin inhibitor 3 (1) | FIAEGHPLSLK | 1211.678251 | 3.0 | 404.564268 |
| 14 | Kunitz trypsin inhibitor 3 (2) | VSDDEFNNYK | 1230.527298 | 2.0 | 615.767287 |
| 15 | Kunitz trypsin inhibitor 1 | DTVDGWFNIER | 1351.627676 | 2.0 | 676.317476 |
| 16 | Gly m Bd 28K | DGPLEFFGFSTSAR | 1530.722300 | 2.0 | 765.864788 |
| 17 | Glycinin precursor | NGLHLPSYSPYPR | 1500.759352 | 3.0 | 500.924635 |
| 18 | 34 kDa maturing seed protein | EESETLVSAR | 1120.548033 | 2.0 | 560.777655 |
| 19 | Gly m 4/PR protein/SAM22 | ALVTDADNVIPK | 1255.689210 | 2.0 | 628.348243 |
| 20 | Gly m 4 | LVAGPNGGSAGK | 1027.553058 | 2.0 | 514.280167 |
| 21 | Gly m 4 | GDAEPNQDELK | 1215.548761 | 2.0 | 608.278019 |

Once synthesized, the peptide internal standard is characterized to develop the targeted, selected reaction monitoring mass spectrometry assay to quantitate this peptide in a biological matrix. In certain embodiments, the internal standards may be characterized individually by mass spectrometry analysis, including tandem mass spectrometry analysis, and also including liquid chromatography-coupled tandem mass spectrometry analysis (LC-MS/MS). The following parameters were determined through characterization: (1) liquid chromatography (LC) retention time; (2) optimal charge state of the stable isotope-labeled peptide; (3) optimal collision energy to fragment the stable isotope-labeled peptide; and (4) suitable product ions (also referred to as "transition") based upon their origins (which part of the peptide they represent) and abundance after fragmentation. These parameters were empirically determined by analyzing the synthetic peptide standards individually, resulting in the instrument being "tuned" to each peptide. That is, the instrument was pre-adjusted according to the pre-selected parameters of the internal standard peptides. In instances where cysteine, methionine, tryptophan, or histidine residues could not be avoided, the peptides were treated as described for the biological sample, and could be variably modified thereby increasing the possible masses by $2^x$ for each of these residues. When spiked into a biological matrix, the labeled (i.e. stable isotope-labeled peptide) and un-labeled (i.e. native) peptide signals had identical retention times but were resolved in the first round of mass analysis.

Using empirically determined peptide masses and retention times, fragment masses for each peptide were discovered and optimized by adjusting the amount of collision energy used by the instrument during fragmentation. The knowledge and information gained through characterizing and monitoring the internal standard peptides provided the instrument with the peptide precursor and fragment masses, the appropriate collision energies and associated retention times, which aided the protein content analysis in a particular sample.

For example, the parameters of peanut and soybean peptide internal standards were listed in Table 3 and 4, respectively.

TABLE 3

Peanut peptide observed masses

| | | unlabeled | | labeled | |
|---|---|---|---|---|---|
| Peptide Name | observed charge (+) | charged peptide mass (Da) | observed fragment masses (Da) | charged peptide mass (Da) | observed fragment masses (Da) |
| Ara h 2 | 3.0 | 542.273051 | 384.0, 720.4, 777.4 | 544.939718 | 388.1, 724.6, 781.5 |
| Ara h 2.02 | 2.0 | 561.248207 | 604.3, 733.4, 846.4 | 566.248207 | 614.4, 743.4, 856.5 |
| Ara h 3/4 | 2.0 | 802.381530 | 375.3, 474.4, 587.4 | 807.381530 | 385.1, 484.4, 597.4 |
| Oleosin | 4.0 | 383.953651 | 375.2, 429.4, 435.4 | 386.453651 | 377.7, 432.8, 438.8 |
| Ara h 6 | 2.0 | 850.321444 | 779.3, 1022.4, 1135.5 | 855.321444 | 789.4, 1032.5, 1145.6 |

TABLE 4

Soybean peptide observed masses

| | | unlabeled | | labeled | |
|---|---|---|---|---|---|
| Peptide Name | observed charge (+) | charged peptide mass (Da) | observed fragment masses (Da) | charged peptide mass (Da) | observed fragment masses (Da) |
| Glycinin G1 | 2.0 | 713.432440 | 425.3, 501.3, 1001.6, 326.2, 904.5, 1100.6, 776.4 | 718.432440 | 425.3, 506.3, 1011.6, 326.2, 914.5, 1110.6, 786.4 |
| Glycinin G2 | 2.0 | 966.463244 | 1390.7, 1276.6, 1147.6, 1018.5, 889.5 | 970.463244 | 1398.7, 1284.6, 1155.6, 1026.6, 897.5 |
| Glycinin G3 | 2.0 | 1116.041992 | 663.3, 791.4, 904.5, 1051.6, 1180.6, 372.2 | 1120.041992 | 671.4, 799.4, 912.5, 1059.6, 1188.6, 380.2 |
| Glycinin G4 | 3.0 | 718.027142 | 854.4, 962.5, 486.3, 1367.7, 1239.6, 1138.6, 740.9, 445.2 | 720.727142 | 858.5, 966.5, 494.3, 1375.7, 1247.6, 1146.6, 744.9, 445.2 |
| Beta-conglycinin, α subunit | 3.0 | 464.629269 | 457.3, 571.3, 670.4, 767.5, 880.5, 951.6, 1064.7, 1165.7 | 467.929269 | 467.3, 581.3, 680.4, 777.5, 890.5, 961.6, 1074.7, 1175.7 |
| Beta-conglycinin, α' subunit | 2.0 | 871.405004 | 500.3, 628.3, 699.4, 814.4, 913.5, 1060.5, 1310.6, | 875.405004 | 508.3, 636.4, 707.4, 822.4, 921.5, 1068.6, 1318.7 |
| Beta-conglycinin, β subunit | 2.0 | 601.306578 | 989.5, 876.4, 819.3, 690.3, 561.3, 1102.5, 432.2, 303.2 | 606.306578 | 999.5, 886.4, 829.4, 700.3, 571.3, 1112.5, 442.2, 313.2 |
| Kunitz trypsin inhibitor 3 (1) | 3.0 | 404.564268 | 460.3, 557.4, 694.4, 751.4, 880.5, 951.5, | 407.264268 | 468.3, 565.4, 702.4, 759.5, 888.5, 959.5 |
| Kunitz trypsin inhibitor 3 (2) | 2.0 | 615.767287 | 1131.5, 1044.4, 685.3, 538.3 | 619.767287 | 1139.5, 1052.4, 693.3, 546.3 |
| Kunitz trypsin inhibitor 1 | 2.0 | 676.317476 | 531.3, 921.5, 678.4, 1036.5, 864.4, | 681.317476 | 541.3, 931.5, 688.4, 1046.5, 874.4 |
| Gly m Bd 28K | 2.0 | 765.864788 | 1148.5, 1019.5, 872.4, 725.4, 1415.7, 1358.7, 1261.6, | 770.864788 | 1158.5, 1029.5, 882.4, 735.4, 1425.7, 1368.7, 1271.6 |
| Glycinin precursor | 3.0 | 500.924635 | 535.3, 619.3, 532.3, 485.2, 966.5, 969.5, | 504.224635 | 535.3, 629.3, 542.3, 485.2, 976.5, 969.5 |
| 34 kDa maturing seed protein | 2.0 | 560.777655 | 432.3, 545.3, 646.4, 862.5, 991.5, 333.2, | 565.777655 | 442.3, 555.3, 656.4, 872.5, 1001.5, 343.2 |
| Gly m 4/PR protein/SAM22 | 2.0 | 628.348243 | 357.2, 456.3, 570.4, 685.4, 756.4, 871.5, 972.5, 1071.6 | 632.348243 | 365.2, 464.3, 578.4, 693.4, 764.4, 879.5, 980.5, 1079.6 |
| Gly m 4 | 2.0 | 514.280167 | 362.2, 419.2, 476.2, 590.3, 687.3, 744.4, 815.4 | 518.280167 | 370.2, 427.2, 484.2, 598.3, 695.3, 752.4, 823.4 |
| Gly m 4 | 2.0 | 608.278019 | 389.2, 504.3, 632.3, 746.4, 843.4, 972.5, 1043.5 | 612.278019 | 397.2, 512.3, 640.3, 754.3, 851.4, 980.5, 1051.5 |

Once the retention time, charge state, collision energy, and transition ions were experimentally determined with the peptide internal standard, and confirmed for the native peptide, the linear range of detection was determined for both the native and stable isotope-labeled peptides in a biological matrix.

In one embodiment, the aforementioned sample obtaining step of the high-throughput method may include the substeps of (a) extracting protein from the seed; (b) dissolving and quantitating protein isolates; (c) digesting the protein into peptides either chemically or enzymatically; and (d) concentrating before mass spectrometry. The plant protein may be isolated through protein extraction process via any suitable methods, such as extraction methods employing phenol, thiourea/urea, urea, or TCA/acetone. However, the extraction methods with phenol yields the highest extraction rate. The resuspension media may be saturated chaotrope solutions like urea or guanidine hydrochloride with various concentrations of detergents to aid membrane protein resuspension.

In the present study, the desiccated seeds were first ground until a uniform powder was formed. The ground seed was mixed with equal portions of Tris-buffered phenol (pH 8.0) and extraction buffer (0.9 M sucrose, 10 mM EDTA, 0.4% 2-mercaptoethanol and 0.1 M Tris-HCl (pH 8.8)) and incubated at 4° C. with inverting for 1 hr. The extraction mix was centrifuged at 5000 g for 30 min to separate the phenol phase. Protein was precipitated by adding 5 volumes 0.1 M ammonium acetate in methanol, and incubating at −20° C. 16 h. The resulting protein was washed free of contaminants using: first, 3×10 ml 100% methanol, 0.1 M ammonium acetate, then 2×10 ml 80% acetone, and followed by 1×10 ml 70% ethanol. The precipitated protein was reconstituted in concentrated urea buffer (8 M Urea, 50 mM TrisHCl pH 8.0) using an appropriate volume of buffer to achieve a concentration of ~1 mg/ml. Protein was quantitated using the Christian-Warburg assay and a "like" pure protein matrix as a reference. For example, total protein is extracted and purified, measured gravimetrically, and aliquoted for use as reference standards. A 10 μg portion of the resulting suspension was aliquoted and diluted to a final volume of 20 μl with 50 mM ammonium bicarbonate, and treated with reducing reagents to break disulfide bonds between cysteines (10 mM dithiothreitol, from a 50 mM stock made in 50 mM ammonium bicarbonate) and alkylating agents to prevent reformation of disulfide bonds (40 mM iodoacetamide, from a 300 mM stock made in 50 mM ammonium bicarbonate) using one hour incubation times for each treatment at room temperature in the dark. The pre-designed internal standard peptides were dissolved in 50% acetonitrile, 1.0% formic acid and mixed together, then added to the protein suspension immediately after initiating digestion with sequencing-grade trypsin using a 1:50 ratio of trypsin to treated protein. Digestion was allowed to proceed 16 hrs at 37° C. The digested protein was then snap frozen with liquid nitrogen and lyophilized.

In the aforesaid analyzing step, the digested protein samples were re-suspended in 5% acetonitrile, 0.1% formic acid and analyzed by LC-MS/MS using nanospray ionization. In still another embodiment, the aforementioned high-throughput method may further comprise determining linear range for quantitation of a representative testing sample. To do so, the following steps were conducted: (a) diluting said testing sample without internal standard peptides serially at a pre-selected range of from 1,000 ng/µl to 1 ng/µl; (b) analyzing said diluted sample using mass spectrometer, thereby monitoring the un-labeled peptide masses and corresponding un-labeled fragment masses; and (c) performing data analysis by plotting intensities for the eluted peptides (summed fragment mass peak areas) as area per ng of peptide analyzed and recording the peak area values that change linearly with respect to quantity loaded (ideally slope=1), thereby providing a linear range window for each peptide. Since all peptides have unique linear ranges, they must be determined empirically. Overlapping linear ranges provide a common load quantity where all peptides can be measured in their linear range of detection.

In still another embodiment, the aforementioned high-throughput method may further comprise determining appropriate molar quantities for the internal standard peptides. To do so, the following steps were conducted: (a) using the common load quantity determined above, "spiking" isotopically-labeled peptide standards into the testing sample in varying amounts according to the preselected range, such as 1,000 fmol to 1 fmol (and outside this range if necessary) to determine the intensity associated with a molar quantity of pure peptide standard; (b) analyzing the sample as described above for un-labeled peptides and monitoring both the unlabeled and labeled precursor and fragment masses; and (c) performing data analysis by plotting the peak area values for the eluted peptides (summed fragment mass peak areas) as per fmol analyzed, and determining the molar quantities of peptide internal standard that were within 10-fold above and below the corresponding un-labeled peptide area values, which were used for further quantitation studies.

To determine the peptide quantities of the testing sample, the following steps were conducted: (a) preparing and aliquoting the testing samples according to the pre-determined common load quantity. Considering the pre-determined molar range for each internal standard peptide, peptides are mixed and aliquoted in appropriate amounts for replicate analyses; (b) analyzing and monitoring the peak areas for un-labeled and labeled peptides; and (c) calculating the ratio of the sum of the un-labeled (endogenous) peptide transition areas to that of the labeled internal standard peptide to obtain the molar quantities for the unlabeled peptide according to the following formula:

$$\frac{\text{Un-labeled peak area (area/ng)}}{\text{Labeled peak area (area/fmol)}} = \text{fmol/ng}$$

The invention also provides a high-throughput method for screening plant allergens within a food supply or product. Such method includes obtaining a protein sample from the food supply; analyzing the sample using mass spectrometry with a set of pre-designed internal standard peptides that are specific to the plant allergens; and monitoring frequencies and intensities of resulting spectra to obtain relative and absolute allergen contents in the food supply. That is, the method of the present invention can be applied to obtain relative and absolute allergen content in a plant seed, and thus be employed as an allergen-screening method for existing or newly developed/discovered plant varieties before they enter into the market.

The invention further provides a system for high-throughput profiling of plant seed allergens. Such system comprises a set of pre-designed internal standard peptides that are specific to the plant seed allergens; and one or more mass spectrometers.

The following specific examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Designing Internal Standard Peptide for Peanut Allergen Oleosin

Spectral counting for proteotypic peptide discovery: A "triple play" experiment using an LTQ-XL linear ion trap mass spectrometer can identify many proteins via their corresponding peptide surrogates. Proteins of interest, discovered during this analysis, may have been identified by multiple peptides from the intact protein (Table 5). Using BLAST, each peptide can be assessed for suitability as an internal standard. The studies in *Arachis hypogaea* identified oleosin (Ara h 10, allergen nomenclature) via the peptides in Table 5. All of the peptides discovered were specific to Oleosin 1 (GenBank Accession #AAU21499), though not all of them are good choices for peptide internal standards. None of the peptides contain cysteines or methionines, but peptides #1-3 have internal trypsin cleavage sites (in bold), which were not desirable. Because one of the peptides (peptide #4, SEQ ID NO:4) was unique (by BLAST analysis) and lacked internal cleavage sites as well as cysteines and methionines, it was chosen to be used as an internal standard.

TABLE 5

Identify Internal Standard Peptide for Oleosin (SEQ ID NO: 4)

| Peptide # | Oleosin Peptides | Identical to: |
|---|---|---|
| 1 | FGDTAAGTNRYPDR (SEQ ID NO: 22) | Oleosin 1 (peanut) |
| 2 | FGDTAAGTNRYPDRGPSTSK (SEQ ID NO: 23) | Oleosin 1 (peanut) |
| 3 | TKEVGQEIQTK (SEQ ID NO: 24) | Oleosin 1 (peanut) |
| 4 | TQPHTVQVHTTAGR (SEQ ID NO: 4) | Oleosin 1 (peanut) |

Example 2

Internal Standard Peptide Characterization and MS Tuning

Figure 1:
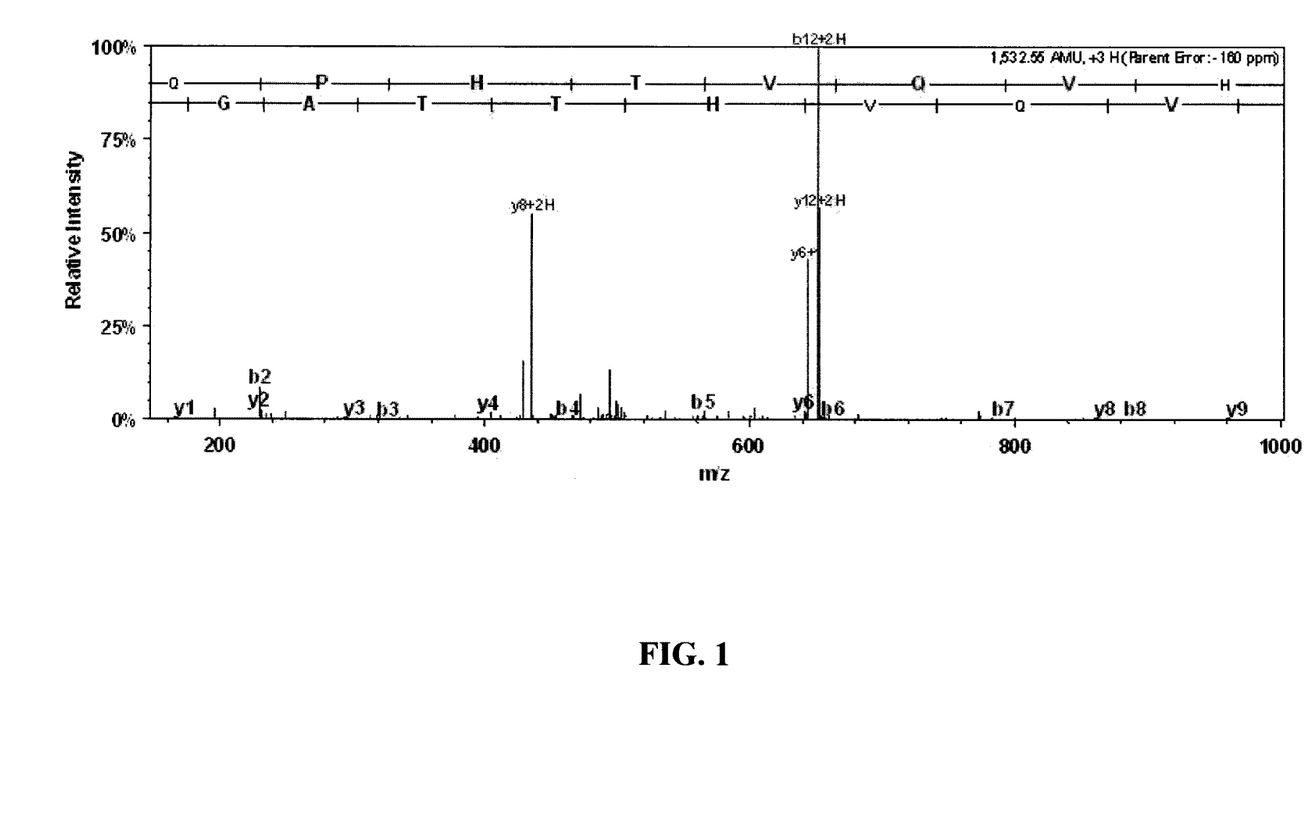
FIG. 1 is a mass spectrometry (MS) spectrum showing Oleosin +3 fragmentation. The vertical lines represent fragment masses created by breaking the +3 charged oleosin peptide during tandem mass spectrometry of a peanut protein digest. Letters across the top indicate the position of fragmentation in the peptide backbone, and labels above the masses correlate to those positions + or − certain adducts.

After deciding on the internal standard peptide for Oleosin 1 (peanut), its retention time and response were characterized. The native peptide has a molecular mass of 1533.6 Da, and the spectral counting experiment showed it has a mass to charge ratio of 511.8, meaning it exists as a +3 charged ion. Its characteristic fragment ions were ascertained. They were measured during the spectral counting experiment as well. An example spectrum is shown in FIG. 1. The vertical lines are the major fragment ion intensity readings which correspond to oleosin peptide fragments.

Figure 2:
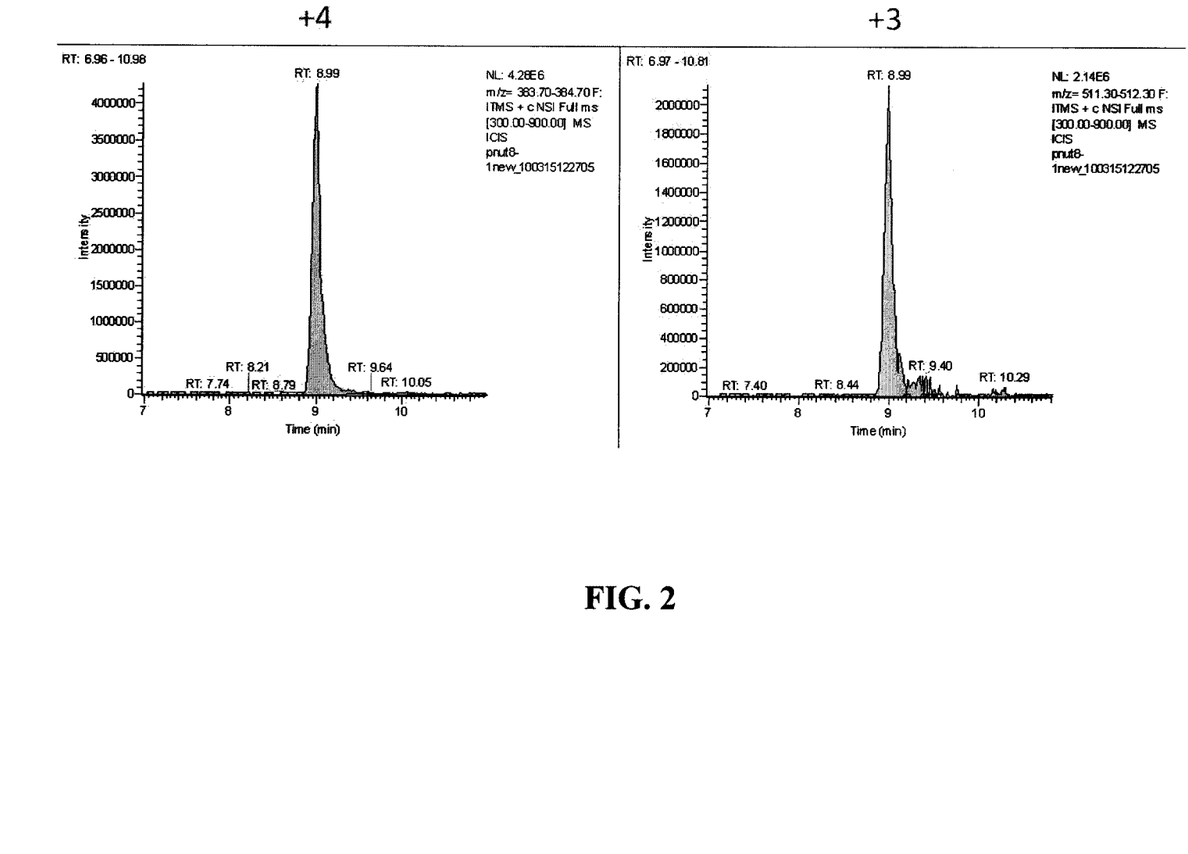
FIG. 2 is a pair of MS1 spectra showing peak comparison between Oleosin +3 and +4. The peaks correlate to the +3 and +4 charge states of the oleosin peptide. The signal from the +4 charge state is twice as intense as that of the +3. Therefore, the +4 charge state should be used for further targeted experiments.

To further characterize this peptide, the oleosin internal standard peptide was analyzed in 2 μg of peanut protein digested with trypsin. Signals for masses correlating to the +3 and +4 charged (can be in two charge states) were examined to decide on which is most intense. The +4 charge state was found to be more intense, as shown in FIG. 2 (the chromatograms), while both are eluting identically, suggesting they are the same peptide.

Figure 3:
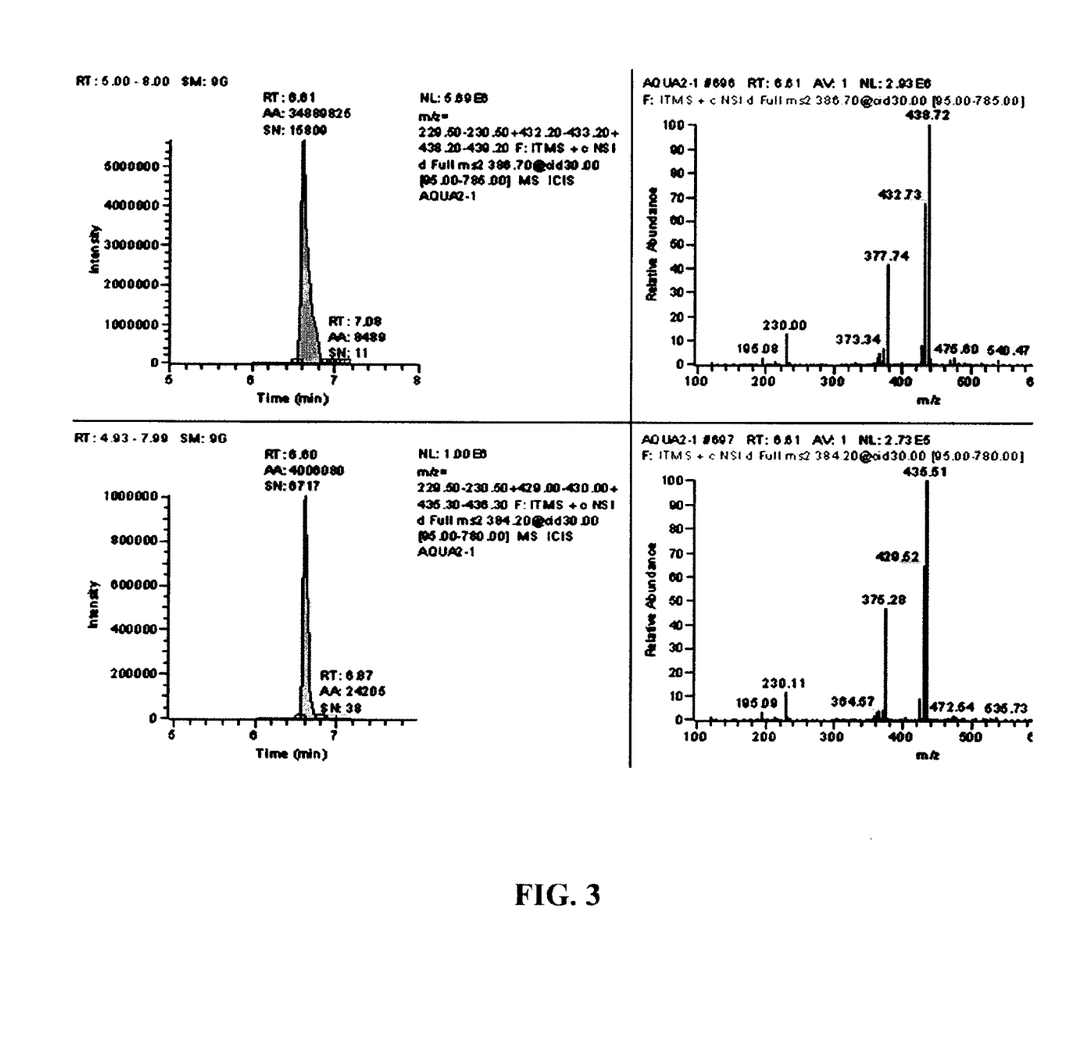
FIG. 3 is a comparison of labeled and un-labeled oleosin peptide MS2 chromatography and corresponding fragment ion spectra. The oleosin peptide is in both the heavy and light form. The top left panel shows the fragment ion signal for the labeled peptide, and the top right shows the corresponding "heavy" fragment ions. Bottom left and right are those for the endogenous "light" peptides.

After deciding on the charge state, the targeted analysis was optimized by tuning the instrument to the oleosin peptide characteristics. This involves infusing the stable isotope-labeled peptide into the instrument and using a semi-automated tuning program in the instrument software. By monitoring the parent mass (in this case 384.2) signal intensity while the ion optics system is adjusted, the transmission of the ion during electrospray ionization can be maximized. Next, fragmentation was optimized using a similar semi-automated tuning program as before, but this time the fragment mass intensities were monitored as the collision energy was adjusted. Once these parameters were adjusted, linearity of response, and labeled peptide standard curves were created to determine the appropriate analyte concentrations for high-throughput, multiplexed quantitation experiments. An example of a signal output for an internal standard-spiked peanut sample is provided in FIG. 3. In this example, both heavy and light peptides were measured and fragmented consecutively in the same analysis, showing identical retention times and isotope shifted masses for parent and fragments.

While the invention has been described in connection with specific embodiments thereof, it will be understood that the inventive device is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

What is claimed is:

1. A method for quantitating plant allergen in a target plant seed, comprising:
   (a) obtaining a protein sample from said target plant seed;
   (b) analyzing said protein sample using mass spectrometry with a set of pre-designed internal standard peptides, wherein said peptides are specific to said plant allergen; and
   (c) monitoring frequencies and intensities of resulting spectra to obtain relative and/or absolute allergen contents in said target plant seed;
   wherein the pre-designed internal standard peptides have a decreased content of cysteines, methionines, tryptophans, and histidines relative to other peptides of the same length specific to said plant allergen; and
   wherein the pre-designed internal standard peptides have a decreased content of internal and adjacent chemical or enzymatic cleavage sites relative to other peptides of the same length specific to said plant allergen.

2. The method of claim 1, wherein said mass spectrometry is tandem mass spectrometry.

3. The method of claim 2, wherein said tandem mass spectrometry is liquid chromatography-coupled tandem mass spectrometry analysis (LC-MS/MS).

4. The method of claim 3, wherein said internal standard peptides are produced by:
   (a) designing stable isotope-labeled peptides specific to said plant allergen;
   (b) synthesizing said peptides; and
   (c) characterizing said peptides individually via liquid chromatography-coupled tandem mass spectrometry analysis (LC-MS/MS).

5. The method of claim 4, wherein said designing step comprises empirical analysis and in silico digestion analysis.

6. The method of claim 4, wherein said synthesizing step comprises synthesizing chemically with a heavy amino acid residue or expressing a synthetic gene in the presence of stable isotope-labeled amino acid(s) or metabolic intermediates.

7. The method of claim 1, wherein said target plant seed is peanut seed, and said internal standard peptides comprise a sequence selected from the group consisting of SEQ ID NOs: 2-4 and a combination thereof.

8. The method of claim 1, wherein said target plant seed is soybean seed, and said internal standard peptides comprise a sequence selected from the group consisting of SEQ ID NOs: 6-21 and a combination thereof.

9. The method of claim 4, wherein said characterizing step comprises determining pre-selected parameters of said peptides, said parameters comprising liquid chromatography (LC) retention time, optimal charge state of said peptides, optimal collision energy to fragment said peptides, and abundance of product ions after fragmentation, said pre-selected parameters presenting the basis for pre-adjusting the instrument for mass spectrometry.

10. The method of claim 1, wherein said obtaining step comprises:
    (a) extracting protein from said target plant seed;
    (b) resuspending and quantitating protein isolates;
    (c) digesting the protein isolates into peptides either chemically or enzymatically; and
    (d) concentrating the digest from step (c) before mass spectrometry.

11. The method of claim 1, further comprising determining linear range for quantitation of a representative testing sample, said determining step comprising:
    (a) diluting said testing sample without internal standard peptides serially at a pre-selected range of from 1,000 ng/µl to 1 ng/µl;
    (b) analyzing said diluted sample using mass spectrometer, thereby monitoring the un-labeled peptide masses and corresponding un-labeled fragment masses; and
    (c) performing data analysis by plotting intensities for eluted peptides as area per ng of peptide analyzed and recording peak area values that change linearly with respect to peptide load quantity, thereby providing a linear range window for each peptide, wherein overlapping linear ranges provide a common load quantity where all peptides can be measured in their linear ranges of detection.

12. The method of claim 11, further comprising determining appropriate molar quantities for said internal standard peptides, said determining step comprising:
    (a) applying isotope-labeled internal standard peptides to said testing sample in varying amounts of 1,000 fmol to 1 fmol;
    (b) analyzing the mixture from (a) using mass spectrometer, thereby monitoring the labeled precursor and fragment masses; and
    (c) performing data analysis by plotting peak area values for the labeled peptides as per fmol analyzed, comparing the peak area values for the labeled peptides vs. the peak area values for corresponding un-labeled peptides, and determining the molar quantities for said labeled peptides that are within 10-fold above and below the corresponding un-labeled peptide area values, said molar quantities are used for further quantitation.

13. A method for screening plant allergens within a food supply, comprising:
    (a) obtaining a protein sample from said food supply;
    (b) analyzing said protein sample using mass spectrometry with a set of pre-designed internal standard peptides, wherein said peptides are specific to said plant allergens; and
    (c) monitoring frequencies and intensities of resulting spectra to obtain relative and/or absolute allergen contents in said food supply;
    wherein the pre-designed internal standard peptides have a decreased content of cysteines, methionines, tryptophans, and histidines relative to other peptides of the same length specific to said plant allergen; and
    wherein the pre-designed internal standard peptides have a decreased content of internal and adjacent chemical or enzymatic cleavage sites relative to other peptides of the same length specific to said plant allergen.

14. The method of claim 13, wherein said food supply includes existing or newly developed/discovered plant varieties.

15. The method of claim 13, wherein said mass spectrometry is tandem mass spectrometry.

16. The method of claim 15, wherein said tandem mass spectrometry is liquid chromatography-coupled tandem mass spectrometry analysis (LC-MS/MS).

17. The method of claim 1, wherein said target plant seed includes genetically-modified plant seeds.

18. The method of claim 14, wherein said plant varieties include genetically-modified plant varieties.

\* \* \* \* \*